United States Patent [19]

Robinson

[11] 4,432,990

[45] Feb. 21, 1984

[54] 5-AMINOIMIDAZOLES AS IMMUNOREGULANTS

[75] Inventor: David Robinson, Shepshed, England

[73] Assignee: Fisons plc, Ipswich, England

[21] Appl. No.: 377,125

[22] Filed: May 11, 1982

[30] Foreign Application Priority Data

May 15, 1981 [GB] United Kingdom ............... 8114895

[51] Int. Cl.³ ................ A61K 31/415; C07D 233/88; C07D 233/90
[52] U.S. Cl. ................................ 424/273 R; 548/301
[58] Field of Search .................... 548/301; 424/273 R

[56] References Cited

U.S. PATENT DOCUMENTS 3,271,398 9/1966 Haraoka et al. ............... 548/301 X
3,586,692 6/1971 Ikehara et al. ..................... 548/301

FOREIGN PATENT DOCUMENTS 51-19770 2/1976 Japan .................................. 548/301

OTHER PUBLICATIONS

Symoens, J., et al., *Springer Semin. Immunopathol.* 2, 49–68 (1979).
Bicker, V., *Augmenting Agents in Cancer Therapy*, Hersh, E., et al., (Editors), Raven Press, New York, 1981, pp. 523–537.
Goutner, A., et al., *New Immunomodulating Agents and Biological Response Modifiers*, Serrov, B., et al. (Editors), Elsevier Biomedical Press, Amsterdam, 1982, pp. 95–112.

*Primary Examiner*—Richard A. Schwartz
*Attorney, Agent, or Firm*—Merriam, Marshall & Bicknell

[57] ABSTRACT

There are described compounds of formula I

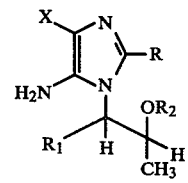

in which X is —CN, —CONH$_2$, —CSNH$_2$,

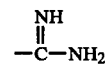

or —CO$_2$R$_3$, R is H or alkyl C 1 to 8, R$_1$ and R$_3$, which may be the same or different, are each alkyl C 1 to 8, and R$_2$ is H or alkanoyl C 2 to 8, and the pharmaceutically acceptable acid addition salts thereof.

There are also described processes for producing the compounds, and pharmaceutical, e.g. immunoregulant, compositions containing them.

9 Claims, No Drawings

5-AMINOIMIDAZOLES AS IMMUNOREGULANTS

This invention relates to new compounds, methods for their preparation and compositions containing them.

According to the invention we provide compounds of formula I,

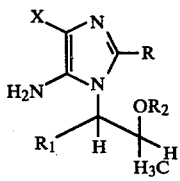   I in which X is —CN, —CONH$_2$, —CSNH$_2$,

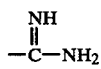

or —CO$_2$R$_3$,

R is H or alkyl C 1 to 8,

R$_1$ and R$_3$, which may be the same or different, are each alkyl C 1 to 8, and R$_2$ is H or alkanoyl C 2 to 8, and pharmaceutically acceptable acid addition salts thereof.

According to the invention we also provide the compounds of formula 1 and pharmaceutically acceptable acid addition salts thereof for use as pharmaceuticals.

According to the invention we further provide a process for the production of a compound of formula I, or a pharmaceutically acceptable acid addition salt thereof, which comprises (a) production of a compound of formula I in which R is as defined above, R$_2$ is H and X is —CN, —CONH$_2$, or —CO$_2$R$_3$ by reaction of a compound of formula II,

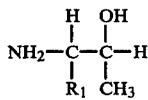   II in which R$_1$ is as defined above, with a compound of formula III,

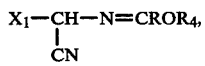   III in which X$_1$ is CN, —CONH$_2$, or —CO$_2$R$_3$, R$_4$ is alkyl C 1 to 8, and R is as defined above, (b) production of a compound of formula I in which R$_2$ is alkanoyl C 2 to 8 by selective alkanoylation of a corresponding compound of formula I in which R$_2$ is H, (c) production of a compound of formula I in which X is —C(=NH)—NH$_2$, by reacting a corresponding compound of formula I in which X is —CN with an alcohol in the presence of an acid, followed by ammonia, (d) production of a compound of formula I in which X is —CSNH$_2$ by reacting a corresponding compound of formula I in which X is —CN with hydrogen sulphide, and if desired or necessary converting the resulting compound of formula I to an acid addition salt thereof or vice versa.

The imidazole formation of process (a) may be carried out in a solvent which is inert under reaction conditions, e.g. acetonitrile, at temperatures ranging from 0° to the reflux temperature of the solvent, e.g. about 80° C.

The alkanoylation of process (b) may be carried out by means of conventional alkanoylation techniques which are designed to alkanoylate a secondary —OH group in the presence of a heterocyclic —NH$_2$. Suitably the reaction may be effected by an acid anhydride, e.g. acetic anhydride, in pyridine at room temperature.

Process (c) may be carried out using alcoholic, e.g. methanolic, acid, e.g. hydrochloric acid, at a temperature lower than ambient temperature, e.g. about −5° to +5° C. followed by treatment with an alcoholic, e.g. ethanolic, solution of ammonia at a temperature of from about 50°–100° C., preferably 90°–100° C.

Process (d) may be carried out using alcoholic, e.g. methanolic, hydrogen sulphide, at a temperature of from about 50° to 100° C. The reaction is preferably carried out in the presence of a base, e.g. potassium hydroxide.

The starting materials for the above processes are either known or may be made from known compounds using conventional techniques known per se.

The compounds of formula I may be recovered from their reaction mixtures using conventional techniques which are known per se.

Pharmaceutically acceptable acid addition salts of the compounds of formula I include salts with pharmaceutically acceptable organic or inorganic anions, e.g. the chloride, sulphate, maleate, p-toluenesulphonate or tartrate anions.

The compounds of formula I, and the pharmaceutically acceptable acid addition salts thereof, are useful because they possess pharmacological activity in animals; in particular they are useful because they possess immunoregulant activity, e.g. in the test set out in Example A. Thus the new compounds are indicated for use in the treatment of auto-allergic diseases including systemic lupus erythematosus, rheumatoid arthritis, Reiter's syndrome, multiple sclerosis, myasthenia gravis, Goodpastures syndrome, glomerulonephritis, ulcerative colitis, Crohn's disease, rheumatic fever, acute heptatitis, primary biliary cirrhosis, autoimmune haemalytic anaemia, idopathic thrombocytopenia purpura, sclerodermas, thyroiditis, orchitis, uveitis, Addison's disease and contact sensitivity; and in the maintenance of allografts, e.g. renal allografts.

For the above mentioned uses the dosage administered will, of course, vary with the compound employed, the mode of administration and the treatment desired. However, in general, satisfactory results are obtained when the compounds are administered at a dosage of from 0.1 to 200 mg per kg of animal body weight in the test set out in Example A. For man the indicated total daily dosage is in the range of from 10 mg to 100 mg and preferably from 50 mg to 500 mg, which may be administered in divided doses from 1 to 6 times a day or in sustained release form. Thus unit dosage forms suitable for administration, e.g. oesophageally, comprise from 2 mg to 500 mg, and preferably 10 mg to 500 mg of the compound preferably admixed with a solid or liquid pharmaceutically acceptable diluent, carrier or adjuvant.

In formula I we prefer R to be hydrogen, $R_1$ to be straight chain alkyl containing 5 to 8 carbons, and X to be $-CONH_2$.

According to our invention we also provide a pharmaceutical composition comprising preferably less than 80%, and more preferably less than 50% by weight of a compound of formula I, or a pharmaceutically acceptable salt thereof, in combination with a pharmaceutically acceptable adjuvant, diluent or carrier. Examples of suitable adjuvants, diluents or carriers are: for tablets, capsules and dragées; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; and for inhalation compositions, coarse lactose. The compound of formula I, or the pharmaceutically acceptable salt thereof, preferably is in a form having a mass median diameter of from 0.01 to 10 microns. The compositions may also contain suitable preserving, stabilising and wetting agents, solubilisers, sweetening and colouring agents and flavourings. The compositions may, if desired, be formulated in sustained release form. We prefer compositions which are designed to be taken oesophageally and to release their contents in the gastrointestinal tract.

The compounds of formula I are asymmetric and may therefore exist in the form of two (or more) optical isomers or a racemic or other mixture of such isomers. The various optical isomers may be resolved, wholly or partially, using conventional techniques. We prefer the erythro form of the compounds.

The invention is illustrated, but in no way limited by the following examples, in which the temperatures are in °C.

EXAMPLE 1

Erythro 5-amino-1-(2-hydroxynon-3-yl)-1H-imidazole-4-carboxamide hydrochloride (a) Erythro 5-amino-1-(2-hydroxynon-3-yl)-1H-imidazole-4-carboxamide A mixture of α-amino-α-cyanoacetamide (4.1 g; 0.04 m) and triethyl orthoformate (6.75 g; 0.046 m) was refluxed in acetonitrile (83 mls) for 45 mins to yield a solution of formimidate. The mixture was cooled, erythro 3-amino-2-nonanol (6.64 g; 0.0417 m) added under nitrogen, and the mixture was stirred for 24 hours. The red solution was filtered and the filtrate evaporated in vacuo to give a red/brown oil. Trituration with ethyl acetate gave the sub-title product as a white solid (4.5 g; 40% yield) which was collected by filtration and dried, mp 159°–160°. The mass spectrum showed M+268 (M.Wt 268)

$C_{13}H_{24}N_4O_2$: Requires: C, 58.19%; H, 9.01%; N, 20.87%. Found: C, 58.43%; H, 8.87%; N, 20.87%.

(b) Erythro 5-amino-1-(2-hydroxynon-3-yl)-1H-imidazole-4-carboxamide hydrochloride The imidazole from (a) above was treated with dilute hydrochloric acid to give the title compound as white crystals, mp 147°–149° C. in 91% yield.

The mass spectrum showed M+268 (M.Wt. of free base 268).

$C_{13}H_{25}N_4O_2Cl$: Requires: C, 51.23%; H, 8.27%; N, 18.38%; Cl, 11.63%. Found: C, 51.63%; H, 8.06%; N, 18.34%; Cl, 11.77%.

EXAMPLE 2

Erythro 5-amino-1-(2-acetyloxynon-3-yl)-1H-imidazole-4-carboxamide hydrochloride (a) Erythro 5-amino-1-(2-acetyloxynon-3-yl)-1H-imidazole-4-carboxamide Acetic anhydride (3.5 g; 0.034 m) was added to a stirred, ice-cooled solution of erythro 5-amino-1-(2-hydroxynon-3-yl)-1H-imidazole-4-carboxamide (5.4 g; 0.02 m) in dry pyridine (20 mls) and the resulting mixture was stirred at room temperature overnight.

Methanol was added and after stirring for 1 hour the solution was evaporated in vacuo to give a yellow oil. The oil, a two component mixture by thin layer chromatography (Silica gel; $CH_2Cl_2/CH_3OH$; 95:5), was purified by preparative high pressure liquid chromatography. Evaporation of the appropriate fractions gave the sub-title product as a white foam (3.35 g).

(b) Erythro 5-amino-1-(2-acetyloxynon-3-yl)-1H-imidazole-4-carboxamide hydrochloride The product of step (a) (3.35 g) immediately above, was dissolved in ethanol (50 mls), cooled in an ice-bath, and one equivalent of 1 M hydrochloric acid was added. The solution was evaporated in vacuo and the residual oil re-dissolved in a minimum of ethanol at 30°. Sufficient ether was added to the stirred ethanolic solution to ensure complete precipitation and after stirring for 24 hours the title compound was obtained as a white solid (3.42 g; 49% overall), mp 179°–181° C.

$C_{15}H_{27}ClN_4O_3$: Requires: C, 51.95%; H, 7.85%; N, 16.15%; Cl, 10.22%. Found: C, 51.82%; H, 7.72%; N, 15.95%; Cl, 10.33%.

The mass spectrum showed M+310 (M.Wt of free base 310).

EXAMPLE 3

Erythro 5-amino-1-(2-hydroxynon-3-yl)-1H-imidazole-4-carbonitrile hydrochloride (a) Erythro 5-amino-1-(2-hydroxynon-3-yl)-1H-imidazole-4-carbonitrile Ammonia was passed into a solution of aminomalonitrile p-toluenesulphonate (20.76 g; 0.082 m) in acetonitrile (700 ml), cooled in an ice/salt bath, for 25 mins. The clear, pale yellow solution was evaporated in vacuo to approximately half volume and filtered. Triethylorthoformate (9.52 g; 10.64 mls; 0.064 m) was added to the filtrate and the solution refluxed for 35 mins under nitrogen.

After cooling the above mixture to 15°, erythro 3-amino-2-nonanol (10 g; 0.063 m) in acetonitrile (25 ml) was added and the red solution stirred at room temperature for 18 hours. Removal of the solvent in vacuo (temp $\leq 30°$) gave a red gum which was partially dissolved in hot ether/ethyl acetate and filtered. The filtrate was evaporated in vacuo and the residue chromatographed on silica gel using ethyl acetate as eluent. Evaporation of the appropriate fractions gave a yellow solid which was triturated with ether and filtered to give the subtitle compound as pale yellow crystals (4.14 g), mp 110°–111°.

(b) Erythro 5-amino-1-(2-hydroxynon-3-yl)-1H-imidazole-4-carbonitrile hydrochloride 0.1 M Hydrochloric acid (20.4 mls) was added to a solution of the above compound (0.51 g) in ethanol (20 ml). Evaporation of the solvent and recrystallisation of the residue from methanol/ethyl acetate gave the title compound as a white solid (0.48 g) mp 173°–174°.

The mass spectrum showed M+250 (M.Wt. of free base 250).

$C_{13}H_{23}ClN_4O$: Requires: C, 54.44%; H, 8.08%; N, 19.53%; Cl, 12.36%. Found: C, 54.58%; H, 7.96%; N, 19.23%; Cl, 12.2%.

EXAMPLE 4

Erythro 5-amino-1-(2-hydroxynon-3-yl)-1H-imidazole-4-carbothioamide

A solution of erythro 5-amino-1-(2-hydroxynon-3-yl)-1H-imidazole-4-carbonitrile (1.02 g; 0.004 m) and potassium hydroxide (0.91 g; 0.163 m) in dry methanol (80 ml) was cooled to 0°, saturated with hydrogen sulphide, and heated to 100° for 5 hours. After cooling to 0°, nitrogen was passed through the solution to remove excess hydrogen sulphide and the residue was evaporated in vacuo to give a yellow solid. This solid was suspended in water and acetic acid added dropwise to pH5. The resulting precipitate was collected by filtration and washed with water. The residue was dissolved in dichloromethane/ethyl acetate, dried ($Na_2SO_4$) and evaporated in vacuo to give a white solid (1.22 g). Recrystallisation from ethyl acetate/charcoal gave a pale yellow solid, which was triturated in ether to give the product as white crystals (0.74 g) mp 170°–171°.

A mass spectrum showed M+284 (M.Wt. 284).

$C_{13}H_{24}N_4OS$: Requires: C, 54.90%; H, 8.5%; N, 19.7%; S, 11.27%. Found: C, 54.78%; H, 8.55%; N, 19.86%; S, 11.56%.

EXAMPLE 5

Erythro 5-amino-1-(2-hydroxynon-3-yl)-2-methyl-1H-imidazole-4-carboxamide

A mixture of ethyl N-(aminocarbonylcyanomethyl)ethanimidate (0.11 g; 0.00065 m) and erythro 3-amino-2-nonanol (0.1 g; 0.00063 m) in dry acetonitrile (5 ml) was stirred at room temperature for 16 hours and filtered. Evaporation of the filtrate in vacuo gave a gum (0.2 g) which was chromatographed on silica gel in methanol/dichloromethane (5:95) to give the product as a white solid (10 mg). The white solid was combined with the products from two further runs and recrystallised from ethyl acetate to give the title compound as white crystals, mp 142°–144°.

The mass spectrum showed M+ 282 (M.Wt. 282).

$C_{14}H_{26}N_4O_2$: Requires: C, 59.6%; H, 9.3%; N, 19.8%. Found: C, 59.6%; H, 9.4%; N, 19.2%.

EXAMPLE 6

Erythro 5-amino-1-(2-hydroxynon-3-yl)-1H-imidazole-4-imidamide hydrochloride

A solution of erythro 5-amino-1-(2-hydroxynon-3-yl)-1H-imidazole-4-carbonitrile (0.2 g) in dry methanol (3.5 ml) was cooled to 0° and saturated with anhydrous hydrogen chloride. The flask was sealed and stored at 0° for four days. Dry either was added to give a white solid which was collected, dried, dissolved in ammonia saturated ethanol (8 ml) and heated at 100° for 2 hours.

After cooling to 0° the solvent was evaporated in vacuo to give the title compound as a colourless gum.

The mass spectrum showed M+ 267 (M.Wt. 267) (15%), 205, 166, 125 (base peak), 108.

EXAMPLE 7

Ethyl erythro 5-amino-1-(2-acetyloxynon-3-yl)-1H-imidazole-4-carboxylate p-toluene sulphonate (a) Ethyl erythro 5-amino-1-(2-hydroxynon-3-yl)-1H-imidazole-4-carboxylate Ethyl α-amino-α-cyanoacetate p-toluene sulphonate (7.4 g; 0.026 m) was stirred in sodium hydroxide solution (0.95 g; 0.024 m in water (12 ml)) for 5 minutes and extracted with chloroform. The chloroform solution was dried ($Na_2SO_4$) and evaporated to give the free base as a yellow oil (1.67 g; 0.013 m).

A solution of the oil and triethylorthoformate (2.17 g; 0.0146 m) in acetonitrile (27 mls) was refluxed for 45 minutes. After cooling to 25°, erythro 3-amino-2-nonanol (2 g; 0.01256 m) was added and the pink solution was stirred at room temperature for 18 hours.

Evaporation of the solvent in vacuo (temp $\leq 30°$) gave a red oil (7.63 g) which was purified by chromatography on silica gel (eluent ethyl acetate) followed by recrystallisation from ethyl acetate/petrol (40°–60°) to give the required compound as a white solid (1.68 g) mp 120°–122°.

The mass spectrum showed M+ 297 (M. Wt. 297)

(b) Ethyl erythro 5-amino-1-(2-acetyloxynon-3-yl)-1H-imidazole-4-carboxylate p-toluene sulphonate Ethyl erythro 5-amino-1-(2-hydroxynon-3-yl)-1H-imidazole-4-carboxylate (1.43 g; 0.0048 m) and acetic anhydride (0.86 g; 0.0084 m) were dissolved in dry pyridine (36 mls) and stirred at room temperature for two days. Ethanol (20 mls) was added and, after stirring for 2 hours, the solvents were removed in vacuo (temp $\leq 30°$). The residue was purified by chromatography on neutral alumina (Brochmann type I, eluent ethyl acetate) to give the product as a yellow gum (0.99 g).

The gum was dissolved in dry ethanol and a solution of p-toluenesulphonic acid (0.55 g; 0.0029 m) in ethanol was added. After stirring for 1 hour, the ethanol was evaporated in vacuo and the residue was triturated in ethyl acetate/ether to give the title compound as a white solid (1.33 g) mpt 137.5°–138.5°.

The mass spectrum showed M+ 339 (M.Wt. of free base 339).

$C_{24}H_{37}N_3O_7S$: Requires: C, 56.34%; H, 7.29%; N, 8.21%; S, 6.27%. Found: C, 56.57%; H, 7.23%; N, 8.08%; S, 6.34%.

EXAMPLE A

The compound of Example 2 has been shown to inhibit a delayed contact sensitivity to oxazolone in mice. This response is a measure of a cell-mediated immune response which is dependent on the activity of thymus-derived lymphocytes. Mice are sensitised with 100 μl of 4.5% oxazolone painted on their abdomen (day 0) and are subsequently challenged with 15 μl of 3% oxazolone on their right ears on day 7. The resulting cell-mediated response is measured 24 hours after challenge by assessing the increase of ear thickness using a dial gauge. The unchallenged left ears act as controls.

Mice receiving a single dose of the compound of Example 2 at 50 mg/kg by the intraperitoneal route, on one of the following days in relation to sensitisation; −1, 0, 1, 2, 3 or 7 show an inhibition of increased ear thickness. Maximum inhibition was seen when the drug was dosed on day 1 when 43% inhibition was observed.

EXAMPLE B

Anti-tumour activity of the compound of Example 1

BDF$_1$ (C57Bl/6×DBA/2) mice grouped in tens were implanted with L1210 leukaemia tumour cells, by intraperitoneal injection, at a concentration of $10^6$ cells. Following implantation one group was injected by the subcutaneous route with the compound of Example 1 at a concentration of 10 mg/kg in polysorbate/saline vehicle, daily for 5 days and subsequently twice weekly for 3 weeks. A control group received injections of vehicle only.

On day 38 following implantation the surviving mice were examined for tumour growth. The results of the test compound treated mice were compared directly to the control mice (Table 1).

|  | Survivors | Bearing tumour | Non-tumour Bearing | Deaths |
| --- | --- | --- | --- | --- |
| Controls (untreated) | 70% | 40% | 30% | 30% |
| Compound of Example 1 treated mice 10 mg/kg | 80% | 20% | 60% | 20% |

The compound of Example 1 has therefore decreased the number of deaths caused by tumours by 33% and increased the number of non-tumour bearing surviving mice by 100%.

I claim:

1. A compound of formula I,

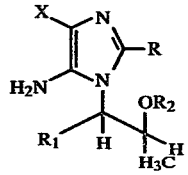

in which X is —CN, —CONH$_2$, —CSNH$_2$,

or —CO$_2$R$_3$,
R is H or alkyl C 1 to 8,
R$_1$ and R$_3$, which may be the same or different, are each alkyl C 1 to 8, and
R$_2$ is H or alkanoyl C 2 to 8,
or a pharmaceutically acceptable acid addition salt thereof.

2. A compound according to claim 1, wherein X is —CONH$_2$.

3. A compound according to claim 1, wherein R$_1$ is C5 to C8 straight chain alkyl group.

4. A compound according to claim 1, wherein the group —R$_1$CH-CH(OR$_2$)CH$_3$ is in the erythro configuration.

5. A compound according to claim 1 and selected from erythro 5-amino-1-(2-hydroxynon-3-yl)-1H-imidazole-4-carboxamide and pharmaceutically acceptable acid addition salts thereof.

6. A compound according to claim 1 and selected from erythro 5-amino-1-(2-acetyloxynon-3-yl)-1H-imidazole-4-carboxamide and pharmaceutically acceptable acid addition salts thereof.

7. A compound according to claim 1 and selected from erythro 5-amino-1-(2-hydroxynon-3-yl)-1H-imidazole-4-carbonitrile,
erythro 5-amino-1-(2-hydroxynon-3-yl)-1H-imidazole-4-carbothioamide,
erythro 5-amino-1-(2-hydroxynon-3-yl)-2-methyl-1H-imidazole-4-carboxamide,
erythro 5-amino-1-(2-hydroxynon-3-yl)-1H-imidazole-4-imidamide,
ethyl erythro 5-amino-1-(2-acetyloxynon-3-yl)-1H-imidazole-4-carboxylate,
and a pharmaceutically acceptable acid addition salt of any one thereof.

8. A pharmaceutical composition for treatment of a condition of the immunoregulatory system involving an auto-allergic component comprising an effective amount of a compound according to any one of the preceding claims in admixture with a pharmaceutically acceptable adjuvant, diluent or carrier.

9. A method of treatment of a condition of the immunoregulatory system involving an auto-allergic component, which comprises administration of an effective amount of a compound according to claim 1 to a patient suffering from such a condition.

* * * * *